United States Patent [19]

Brisebois

[11] Patent Number: 5,718,699
[45] Date of Patent: Feb. 17, 1998

[54] DISPOSABLE ABSORBENT PRODUCT WITH SECONDARY LIQUID-CONTAINMENT STRUCTURE

[75] Inventor: Henri Brisebois, Lachenaie, Canada

[73] Assignee: Johnson & Johnson, Inc., Montreal, Canada

[21] Appl. No.: 652,258

[22] Filed: May 23, 1996

Related U.S. Application Data

[63] Continuation-in-part of Ser. No. 318,003, Oct. 4, 1994, abandoned.

[51] Int. Cl.$^6$ .................................................. A61F 13/15
[52] U.S. Cl. ...................... 604/385.1; 604/378; 604/387
[58] Field of Search ................................ 604/387, 389, 604/385.1, 385.2, 378

[56] References Cited

U.S. PATENT DOCUMENTS

| | | | |
|---|---|---|---|
| 3,595,235 | 7/1971 | Jespersen | 604/378 |
| 4,285,343 | 8/1981 | McNair | 604/387 |
| 4,425,130 | 1/1984 | DesMarais | 604/389 |
| 4,687,478 | 8/1987 | VanTilburg | 604/387 |
| 4,701,178 | 10/1987 | Glaug et al. | 604/387 |
| 4,963,139 | 10/1990 | Dabroski | 604/378 |
| 5,133,704 | 7/1992 | Wheeler | 604/387 |
| 5,133,705 | 7/1992 | Nakanishi et al. | 604/387 |
| 5,201,727 | 4/1993 | Naanishi et al. | 604/390 |
| 5,275,591 | 1/1994 | Marvinkurve | 604/387 |
| 5,429,633 | 7/1995 | Davis et al. | 604/387 |

*Primary Examiner*—David H. Willse
*Assistant Examiner*—David J. Cho
*Attorney, Agent, or Firm*—James P. Barr

[57] ABSTRACT

A disposable absorbent product such as a sanitary napkin, a diaper, an adult disposable brief or an urinary pad, among others, including a liquid-permeable cover layer, and absorbent core and a liquid-impervious layer for preventing body exudate entrapped in the absorbent core from contacting the wearer's undergarment or skin. A secondary liquid containment structure for intercepting body exudate leaking past the side edges of the absorbent product is mounted underneath the liquid-impervious layer. The containment structure includes a transversely extending strip of absorbent material such as non-woven fabric, having longitudinal end portions forming liquid-acquisition zones. The central portion of the absorbent strip constitutes a reservoir layer for collecting the body exudate discharged on the liquid-acquisition zones. In a preferred embodiment, the longitudinal end portions of the strip are sufficiently long to form tabs capable of being folded about the edges of the undergarment for stabilizing the absorbent product against the perineal region of the wearer.

32 Claims, 3 Drawing Sheets

DISPOSABLE ABSORBENT PRODUCT WITH SECONDARY LIQUID-CONTAINMENT STRUCTURE

This is a Continuation-In-Part Application of commonly assigned application Ser. No. 08/318,003, filed Oct. 4, 1994, now abandoned.

FIELD OF THE INVENTION

The invention relates to the art of manufacturing structures for absorbing body exudate. More specifically, the invention relates to a disposable absorbent product including a secondary liquid-containment structure for intercepting stray liquid droplets that leaking past the side edges of the absorbent product.

BACKGROUND OF THE INVENTION

Experimental procedures conducted on sanitary napkin designs have demonstrates that product failures can often be traced to the inability of the cover layer that contacts the perineal region of the wearer to capture on contact the discharge of body exudate. If liquid is allowed to remain on the cover layer for an extended period of time droplets are likely to run-off on the surface of the cover layer and leak past the edge of the sanitary napkin. The precise point of leakage depends primarily upon the posture of the wearer; when she lies horizontally, the gravitational forces induce the liquid to travel longitudinally on the sanitary napkin and to accumulate on the rear longitudinal end portion. To avoid saturation and overflow leakage at that area, products with improved absorbency at the critical site have been developed during the past recent years. An example is the sanitary napkin available from Johnson & Johnson Inc. under the trade designation STAYFREE PRIMA Ultra Thin/Long Maxi. This product features a long body that progressively widens toward the rear so as to offer an increased liquid-acquisition surface area.

In contrast, sanitary napkins designed primarily for daytime leak mostly at the sides because the posture of the wearer is such that the liquid has a propensity to accumulate in the central area of the napkin that is reduced in width due to compressive loading exerted by the thighs. As a consequence, a much smaller surface area is made available to the liquid for penetrating the absorbent structure.

In theory, the incidence of product failure at the side edges could be reduced by increasing the width of the sanitary napkin. However, this solution is marginal at best because the added material will negatively affects the comfort potential of the product by creating undue pressure against the thighs. In addition, regardless on any comfort issues, the width increase is unlikely to bring about any material improvement in leakage protection because the lateral compression by the thighs would still reduce by a great measure the effective liquid-acquisition surface area.

OBJECTIVE AND STATEMENT OF THE INVENTION

An object of the invention is a disposable absorbent product as a sanitary napkin, a diaper, an adult disposable brief or an urinary pad, among others, offering an enhanced protection against leakage at the side edges.

As embodied and broadly described herein, the invention provides a disposable absorbent product, comprising:

a primary liquid-containment structure having longitudinally extending side edges and transversely extending end portions, said primary liquid-containment structure, including:
  a) an absorbent core;
  b) a liquid-impervious layer underneath said absorbent core;

a secondary liquid-containment structure secured to said primary liquid-containment structure at a location intermediate said transversely extending end portions, said location being adjacent to a center of said primary liquid-containment structure, said secondary liquid-containment structure having a dimension measured along a longitudinal axis of said primary liquid-containment structure less than a longitudinal dimension of said primary liquid-containment structure, said secondary liquid-containment structure including:
  a) a reservoir zone positioned underneath said liquid-impervious layer;
  b) a pair of liquid-acquisition zones located in adjacency to respective longitudinally extending side edges of said primary liquid-containment structure, said liquid-acquisition zones being in liquid-communicative relationship with said reservoir zone, whereby said liquid-acquisition zones are capable of intercepting body exudate leaking past said side edges and then transfer the body exudate to said reservoir layer.

The advantages of this absorbent structure are immediately apparent. Droplets of menstrual liquid that leak past the side edges of the sanitary napkin, that constitutes the primary liquid-containment structure are collected by the liquid-acquisition zones and then transferred to the reservoir zone of the secondary liquid-containment structure for permanent storage. Accordingly the incidence of failure of the sanitary napkin is significantly diminished.

The expression "liquid-acquisition zones located in adjacency to respective side edges . . ." appearing in the specification and claims is intended to mean that the liquid-acquisition zones are positioned close enough to the side edges so as to intercept body exudate that may leak past the side edges. In one embodiment, the liquid-acquisition zones project beyond the side edges to catch falling drops of body exudate. For applications designed to handle body exudate of more viscous nature, such as menstrual liquid, the liquid-acquisition zones may be flush with the side edges or slightly recessed from the side edges. Note that most viscous liquids develop a strong interfacial tension with the supporting substrate. Consequently, a menstrual liquid runoff on the cover layer of a sanitary napkin will have a tendency to accumulate on the side edge or immediately underneath (on the liquid-impervious layer), rather than immediately dripping off. Thus, a slightly recessed liquid-acquisition zone will still establish contact with the escaping liquid.

In a preferred embodiment, the secondary liquid containment structure includes an elongated strip of absorbent material, such as a non-woven fabric, laminated with a film of plastic material. The film of plastic material constitutes a barrier layer for preventing liquid entrapped in the absorbent strip from staining the undergarment of the wearer. The longitudinal end portions of the elongated absorbent strip constitute the liquid-acquisition zones provided to capture droplets of body exudate leaking past the side edges of the disposable absorbent product. Most preferably, the liquid-acquisition zones are sufficiently long to form tabs that can be folded about the edges of the undergarment and adhesively secured to the garment facing surface of the undergarment, thus stabilizing the disposable absorbent product against the perineal region of the wearer.

As embodied and broadly described herein, the invention further provides a disposable sanitary napkin, comprising:

a liquid-pervious cover layer for contacting a perineal region of the wearer;

an absorbent core underneath said liquid-pervious cover layer;

a liquid-impervious layer underneath said absorbent core, said liquid-impervious layer including longitudinally extending side edges;

a secondary liquid containment structure including an elongate strip of absorbent material mounted underneath said liquid-impervious layer, said elongate strip of absorbent material being secured to said liquid-impervious layer adjacent to a center of said liquid-impervious layer, said strip of absorbent material being oriented generally transversally to a longitudinal axis of said liquid-impervious layer and projecting beyond respective side edges of said liquid-impervious layer to form liquid-acquisition zones capable of capturing body exudate leaking past either one of said side edges, a portion of said strip of absorbent material intermediate said liquid-acquisition zones constituting a reservoir area for collecting body exudate taken-up by said liquid-acquisition zones.

As embodied and broadly described herein, the invention further provides a disposable absorbent product, comprising:

a primary liquid-containment structure having longitudinally extending side edges and transversely extending end portions, said primary liquid-containment structure, including:
 a) an absorbent core;
 b) a liquid-impervious layer underneath said absorbent core;

a secondary liquid-containment structure secured to said primary liquid-containment structure at a location intermediate said transversely extending end portions, said secondary liquid-containment structure having a dimension measured along a longitudinal axis of said primary liquid-containment structure less than a longitudinal dimension of said primary liquid-containment structure, said secondary liquid-containment structure including:
 a) a reservoir zone positioned underneath said liquid-impervious layer;
 b) a pair of liquid-acquisition zones located in adjacency to respective longitudinally extending side edges of said primary liquid-containment structure, said liquid-acquisition zones being in liquid-communicative relationship with said reservoir zone, whereby said liquid-acquisition zones are capable of intercepting body exudate leaking past said side edges and then transfer the body exudate to said reservoir layer; and
 c) longitudinal end portions of said secondary liquid-containment structure projecting beyond the longitudinal side edges of said primary liquid-containment structure, said longitudinal end portions being foldable about edges of an undergarment and providing means for enhancing a stability of said primary liquid-containment structure with relation to the undergarment; and
 d) said liquid-acquisition zones being located on said longitudinal end portions.

BRIEF DESCRIPTION OF THE DRAWINGS

Identical or similar components throughout the drawings are designated by the same reference numerals.

DESCRIPTION OF PREFERRED EMBODIMENTS

The present invention provides a disposable absorbent product such as a sanitary napkin, a diaper, an adult disposable brief or a urinary pad, among others, featuring a secondary liquid containment structure for intercepting small amounts of body exudate that may leak past the side edges of the disposable absorbent product and cause stains on the wearer's undergarment.

Figure 1:
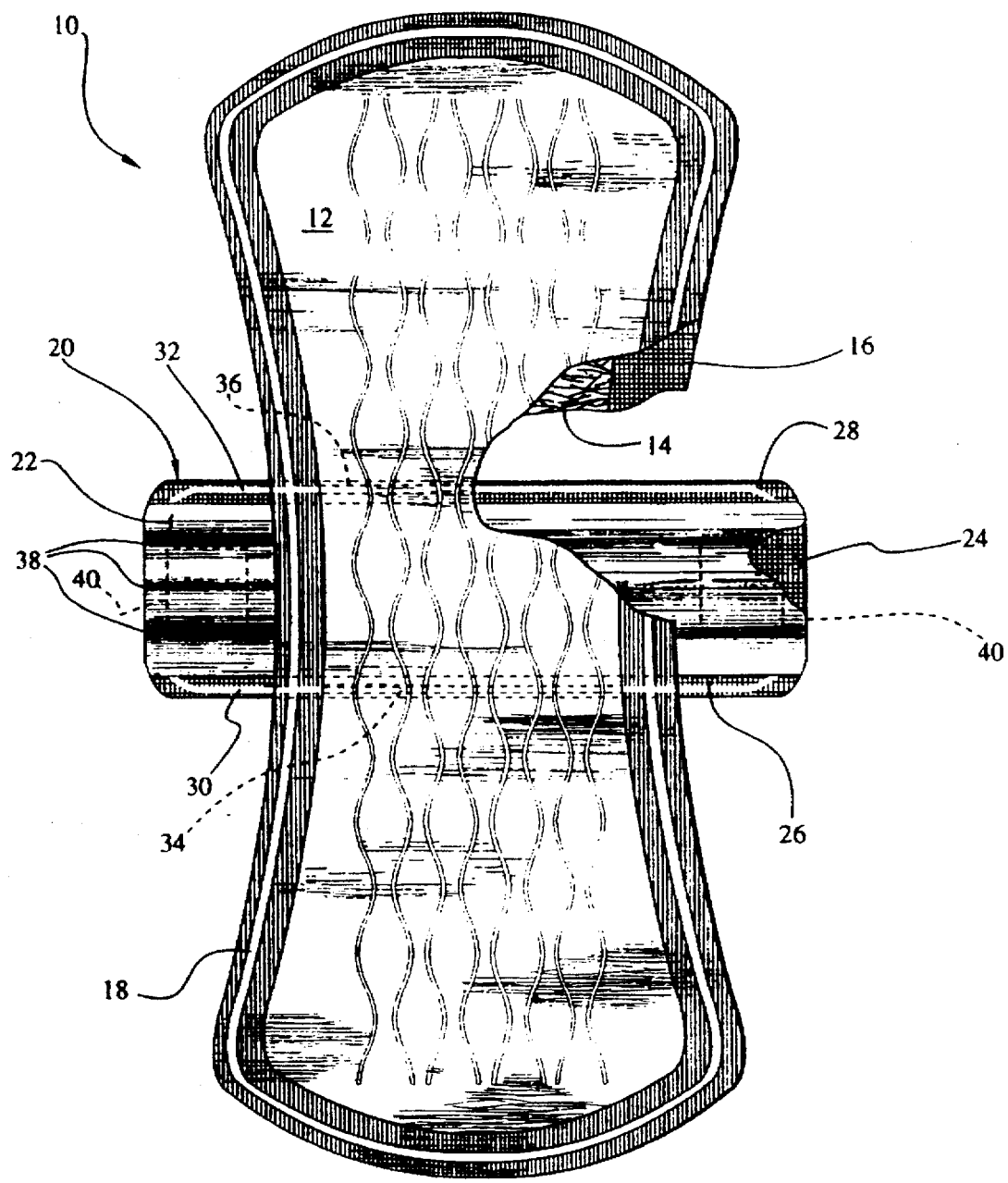
FIG. 1 is a fragmentary top plan view of a sanitary napkin in accordance with the invention.

FIG. 1 illustrates a sanitary napkin embodying the principles of this invention. The sanitary napkin is designated comprehensively by the reference numeral 10 and comprises a liquid-permeable cover layer 12 that in use contacts the perineal region of the wearer. The cover layer 12 is made of a fibrous material, such as a non-woven fabric. Alternatively, an apertured polymeric film can be used. Underneath the cover layer 12 is provided an absorbent core 14 designed to collect the discharge of body exudate delivered on the cover layer 12. The absorbent core 14 may be of any suitable construction designed to meet the absorbency requirements of the sanitary napkin 10. Most preferably, the absorbent core 14 is a multi-layered structure comprising an upper transfer layer in an intimate fluid communicative relationship with a lower reservoir layer. The transfer layer is a highly porous structure capable of fast liquid acquisition, thus enabling the sanitary napkin 10 to capture on contact a discharge of body exudate. On the other hand, the reservoir layer has a much finer porosity so the liquid temporarily held in the transfer layer is induced to migrate in the reservoir layer under the effect of capillary attraction, where it is permanently stored.

Underneath the absorbent core 14 is provided a liquid-impervious layer 16 made of polymeric film such as polyethylene. The purpose of the liquid-impervious layer 16 is to prevent body exudate entrapped in the absorbent core 14 from egressing the garment facing surface the sanitary napkin 10.

The cover layer 12 and the liquid-impervious layer 16 are joined to one another for the purpose of completely enclosing the absorbent core 14. Most preferably, the joint is made by thermally bonding the cover layer 12 and the liquid-impervious layer 16 along a continuous seal line 18 that extends slightly inwardly of the peripheral edge of the sanitary napkin 10.

The sanitary napkin 10 is characterized by a secondary liquid-containment structure 20 provided to capture stray droplets of menstrual liquid that leak past the side edges of the napkin 10 and may, if allowed to escape, stain the undergarment of the wearer. The liquid containment structure 20 includes an elongated strip 22 of fibrous material extending underneath the liquid-impervious layer 16. The material of choice for manufacturing the absorbent strip 22 is a non-woven fabric made of natural or synthetic fibers that are preferably hydrophilic, such as cellulose fibers, rayon fibers or cotton fibers. It is also possible to use an apertured polymeric film rather than a fibrous medium.

The absorbent strip 22 is laminated with a barrier layer 24 made of suitable liquid-impervious material. Polyethylene is a suitable material. The barrier layer 24 is co-extensive with the absorbent strip 22 to prevent the liquid in storage therein from entering in contact with the user's undergarments. In a preferred mode of construction, the longitudinal extremities of the barrier layer 24 are folded over the absorbent strip 22, providing two longitudinally extending narrow bands 26 and 28 in overlaying relationship with the absorbent strip 22. Continuous heat-seal lines 30 and 32 unite the barrier layer 24 and the absorbent strip 22 in a functional whole. It will be apparent that the heat-sealing operation requires the presence in the absorbent strip 22 of material that can be reduced to a plastic state by the application of heat, such as low melt polymeric fibers or thermoplastic binder. Such thermobondable component also has the advantage of consolidating the fibrous network by establishing a multiplicity of internal inter-fiber bonds during the heat-sealing operation.

The secondary liquid-containment structure 20 is secured to the liquid-impervious layer 16 by transversely extending heat-seal lines 34, 36 (with respect to the longitudinal axis of the sanitary napkin 10) that are coincident with the heat-seal lines 30 and 32. In a most preferred embodiment the a heat-seal lines 30, 32 and 34, 36 are formed in a single operation so as to simultaneously bond the barrier layer 24 to the absorbent strip 22 and the entire liquid-containment structure 20 the liquid-impervious layer 16.

The above described arrangement has the effect of separating the absorbent strip 22 in two functional elements namely a reservoir zone that extends underneath the sanitary napkin 10 and a pair of liquid-acquisition zones located in the vicinity of the respective side edges of the sanitary napkin 10. It will be apparent that the reservoir zone functions as a independent and self-contained absorbent component, totally isolated from the main absorbent core 14 by the liquid-impervious layer 16.

Note the presence of an uninterrupted capillary path from each liquid-acquisition zone toward the reservoir zone that allows liquid collected by either one of the liquid-acquisition zones to migrate toward the reservoir zone where it is confined between two layers of impervious material (the liquid impervious layer 16 and the barrier layer 24) so as to remain isolated from the user's undergarment and skin. The pattern of heat-sealing lines used for joining the liquid-containment structure 20 to the liquid-impervious layer 16 is of importance with regard to the integrity of this capillary pathway. For instance, a continuous seal line that extends transversally with relation to the liquid-absorbent strip 22 should be avoided because it may have the effect of creating a barrier to the migration of liquid toward the reservoir zone. The most preferred sealing pattern includes a pair of bonding sites, such as the heat-seal lines 32, 34 that are in a spaced apart relationship. With this arrangement, liquid absorbed by the liquid-acquisition zones is transferred to the reservoir layer by migrating between the bonding sites.

To induce the liquid collected by the liquid-acquisition zones to travel longitudinally on the strip 22 and thus migrate toward the reservoir zone, longitudinal densification lines 38 are provided on the absorbent strip 22. The densification lines 38 are essentially strip-like areas where the fibrous matrix has been mechanically compacted to create a network of reduced pore size that provides a preferential liquid pathway.

In the embodiment illustrated in FIG. 1 the longitudinal end portions of the liquid-containment structure 20 are extended to a significant degree beyond the side edges of the sanitary napkin 10 to form tab structures that can be folded about the edges of the undergarment to stabilize the sanitary napkin 10 against the perineal region of the wearer. At this end, adhesive zones 40 (shown in dotted lines) are provided on the barrier layer 24 to releasably bond the longitudinal end portions of the absorbent strip 22 that are in a folded condition to the garment facing surface of the wearer's underpants. In this embodiment, the liquid-containment structure 20 provides a structural function by enhancing the stability of the sanitary napkin 10 in addition to the leakage protection feature.

Figure 2:
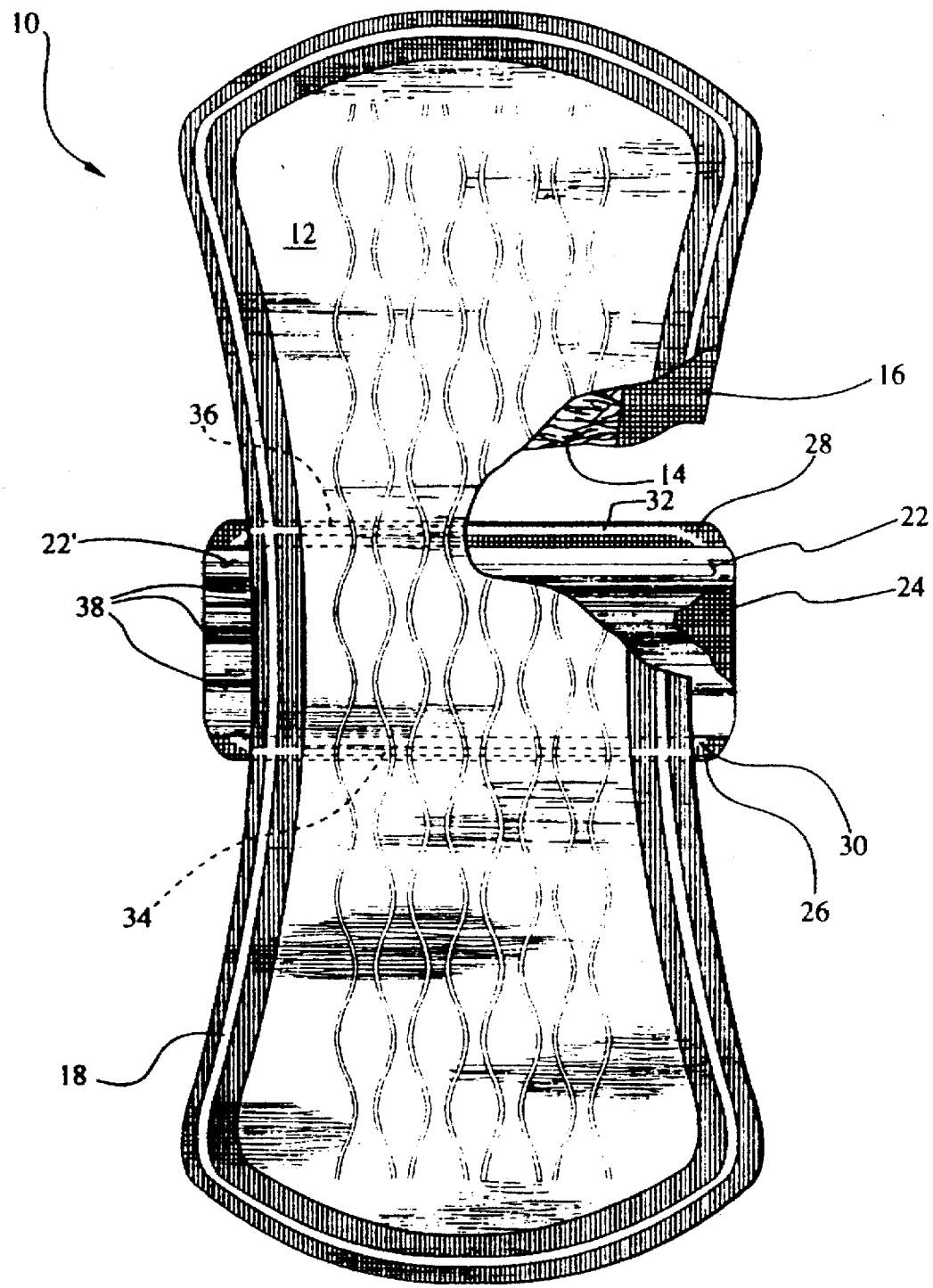
FIG. 2 is a fragmentary top plan view of a sanitary napkin in accordance with a variant.
Figure 3:
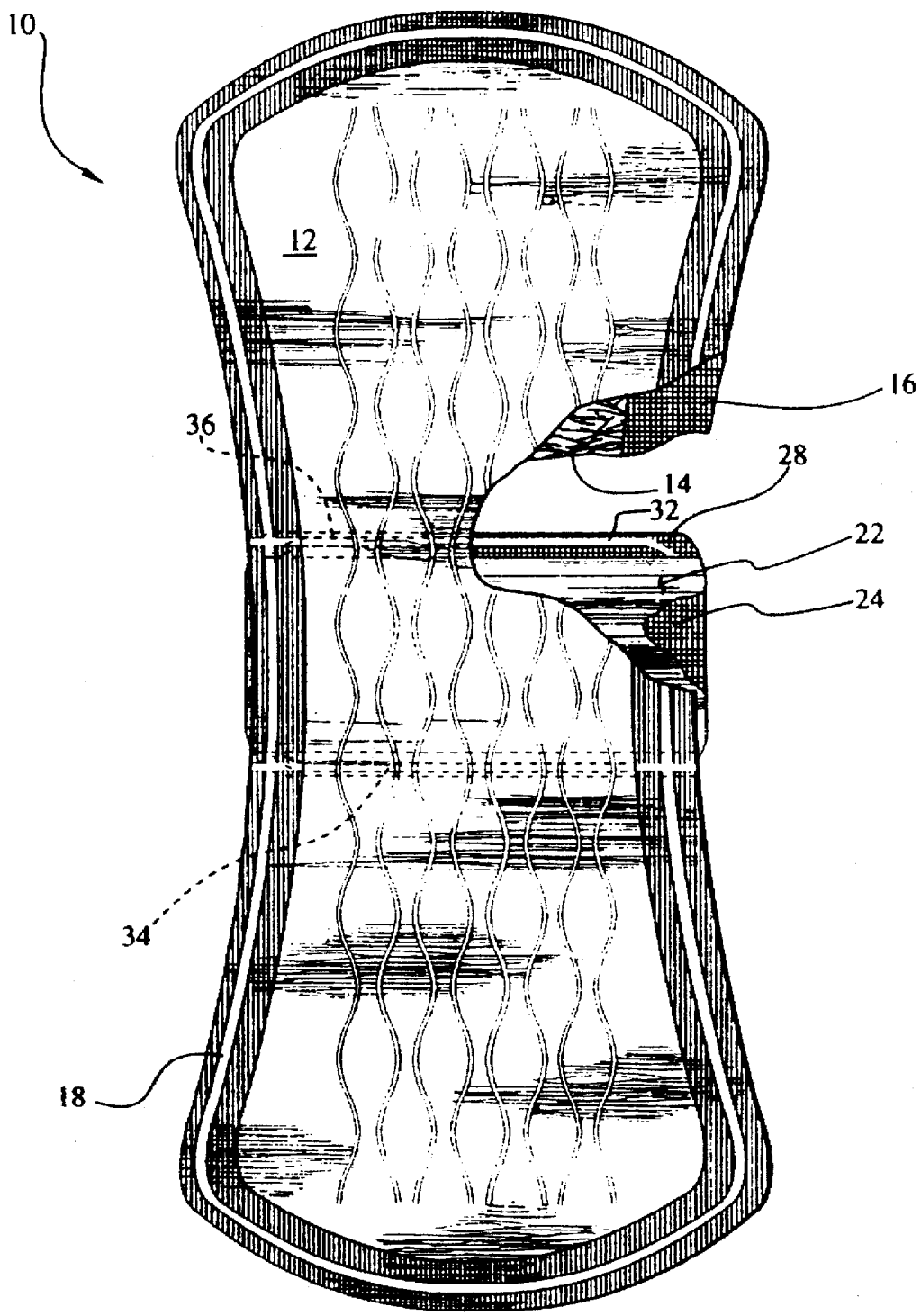
FIG. 3 a top plan view of a sanitary napkin in accordance with a further variant.

FIG. 2 illustrates a variant of the sanitary napkin 10. The difference with the previously described embodiment resides in that the liquid-containment structure is significantly reduced in length and no longer provides a stabilization activity. Here, the absorbent strip 22' extends beyond the side edges of the sanitary napkin by a short distance, in the order of a few millimeters. In a further variant the longitudinal extremities of the absorbent strip 22' may be flush with the side edges of the sanitary napkin, as shown in FIG. 3, or even slightly recessed (not shown in the drawings). It should be pointed out that the liquid-containment structure is not intended to be a high capacity device as in practice it will be required to handle but a few droplets of menstrual liquid at a time. Since menstrual liquid is a highly viscous media it develops a comparatively high interfacial tension with the supporting substrate. Accordingly, when a drop of menstrual liquid that travels in a transverse direction on the cover layer 12 reaches the side edge of the sanitary napkin the interfacial tension will prevent it from freely dropping off. Rather, the drop will have a tendency to remain suspended from the side edge which then brings it in contact with the liquid acquisition zone even when the liquid-acquisition zone is in a somewhat recessed condition with relation to the side edge.

The following test conducted on sanitary napkins embodying the principles of this invention demonstrates the usefulness of the secondary liquid-containing structure in reducing the incidence of failures as a result of side leakage.

Six sanitary napkin samples were prepared for the purpose of the test, along with a control sample. The control sample is a sanitary napkin available from Johnson & Johnson under the brand designation STAYFREE PRIMA MAXI without tabs. Samples 1, 2 and 3 are control samples modified by attaching to the liquid-impervious layer a liquid-containment structure that extends beyond each side edge of the sanitary napkin by a distance of 3 millimeters (mm). The resulting structure is identical to the embodiment depicted in FIG. 2. In sample 1 the absorbent strip of the liquid-containment structure is made from absorbent material available from Walkisoft Corporation under the brand designation WAKISOFT. This material is a blend comprising cellulosic fibers and binder in a ratio 4/1 respectively, by weight. The basis weight of the absorbent strip is of 48 grams per square meter (g/m$^2$). The absorbent strip used in sample 2 is identical to sample 1 except that the basis weight is increased to 97 g/m$^2$. Sample 3 uses an absorbent strip made of material available from James River Corporation under the brand name AIRTEX. This material includes cellulosic fibers (82% by weight) and latex binder (18% by weight) and it has a basis weight of 120 g/m$^2$.

Samples 4, 5 and 6 are identical to samples 1, 2 and 3 respectively, except that the liquid-containment structure is cut shorter so it is totally flush with the side edges of the sanitary napkin, as shown in FIG. 3.

The test procedure consist of placing the side edge of the sample oriented at 45 degrees in contact with a horizontally extending glass plate. One cubic centimeter of synthetic menstrual liquid without protein (viscosity of 5 centipoise) is delivered with a syringe at the linear interface sample/ glass plate, in the region of the liquid-acquisition zone. After 20 seconds the liquid on the glass plate is wiped with absorbent paper. The wetted absorbent paper is weighed and the dry weight is subtracted from the measured value to determine the weight of the liquid uptake. This value is then subtracted from the weight of the total liquid discharge (1.064 grams) to determine the amount of liquid taken up by the liquid-containment structure.

The results are summarized in the following table

| MATERIAL TESTED | AMOUNT OF LIQUID ABSORBED grams (g) |
| --- | --- |
| Sample 1 | 1.00 |
| Sample 2 | 1.03 |
| Sample 3 | 1.03 |
| Sample 4 | 1.05 |
| Sample 5 | 1.03 |
| Sample 6 | 1.05 |
| Control | Virtually nil |

The test clearly shows that the liquid-containment structure was capable of absorbing in all six cases (samples 1 to 6) almost the entire liquid discharge simulating the side failure. In contrast, the control was totally unsuccessful in containing the liquid discharge.

The scope of the present invention is not limited by the description, examples and suggestive uses herein, as modifications can be made without departing from the spirit of the invention. Thus, it is intended that the present application covers the modifications and variations of this invention provided that they come within the scope of the appended claims and their equivalents.

I claim:

1. A disposable absorbent product, comprising:
   a primary liquid-containment structure having longitudinally extending side edges and transversely extending end portions, said primary liquid-containment structure, including:
   a) a liquid pervious cover layer constituting a body-facing surface;
   b) an absorbent core;
   c) a liquid-impervious layer underneath said absorbent core for preventing body exudate entrapped in said absorbent core from egressing therefrom and constituting a garment-facing surface;
   the liquid-pervious cover layer and the liquid impervious layer being joined to one another to completely enclose the absorbent core;
   a secondary liquid-containment structure secured to said outer garment facing surface of the liquid impervious layer at a location intermediate said transversely extending end portions, said location being adjacent to a center of said primary liquid-containment structure, said secondary liquid-containment structure having a dimension measured along a longitudinal axis of said primary liquid-containment structure substantially less than a longitudinal dimension of said primary liquid-containment structure, said secondary liquid-containment structure including:
   a) a reservoir zone positioned underneath said liquid-impervious layer;
   b) a pair of liquid-acquisition zones located in adjacency to respective longitudinally extending side edges of said primary liquid-containment structure, said liquid-acquisition zones being in liquid-communicative relationship with said reservoir zone, whereby said liquid-acquisition zones are capable of intercepting body exudate leaking past said side edges and then transfer the body exudate to said reservoir layer.

2. A disposable absorbent product as defined in claim 1, wherein each said liquid-acquisition zone is positioned underneath said liquid-impervious layer.

3. A disposable absorbent product as defined in claim 1, wherein each said liquid-acquisition zone extends laterally beyond the respective side edge.

4. A disposable absorbent product as defined in claim 1, wherein each said liquid-acquisition zone is generally flush with the respective side edge.

5. A disposable absorbent product as defined in claim 1, comprising a capillary continuum between said liquid-acquisition zones and said reservoir zone, said capillary continuum allowing body exudate intercepted by said liquid-acquisition zones to migrate toward said reservoir zone.

6. A disposable absorbent product as defined in claim 5, wherein said secondary liquid-containment structure is bonded to said liquid-impervious layer at two sites in a spaced apart relationship.

7. A disposable absorbent product as defined in claim 6, wherein said capillary continuum passes between said sites.

8. A disposable absorbent product as defined in claim 1, comprising a layer of porous material underneath said liquid-impervious layer, an end portion of said layer of porous material constituting one of said liquid-acquisition zones, an area of said layer of porous material contiguous with said end portion constituting said reservoir zone.

9. A disposable absorbent product as defined in claim 8, comprising a barrier layer underneath said layer of porous material.

10. A disposable absorbent product as defined in claim 8, wherein said layer of porous material extends generally transversally to a longitudinal axis of said primary liquid-containment structure.

11. A disposable absorbent product as defined in claim 8, wherein said layer of porous material includes a localized area of reduced average pore size extending from one of said liquid-acquisition zones toward said reservoir zone, said localized area of reduced average pore size manifesting a high capillary attraction to induce liquid captured by said one liquid-acquisition zone to migrate toward said reservoir zone.

12. A disposable absorbent product as defined in claim 11, wherein said layer of porous material includes a densified region forming said localized area of reduced average pore size.

13. A disposable absorbent product as defined in claim 12, comprising a plurality of densified regions extending longitudinally on said layer of porous material.

14. A disposable absorbent product as defined in claim 8, wherein said layer of porous material includes fibers selected from the group consisting of cellulosic fibers, rayon fibers and cotton fibers.

15. A disposable absorbent product as defined in claim 8, wherein said layer of porous material is a non-woven fabric.

16. A disposable absorbent product as defined in claim 8, wherein said layer of porous material is an apertured polymeric film.

17. A disposable absorbent product as defined in claim 9, wherein said barrier layer is folded over each longitudinal edge of said layer of porous material to form a pair of bands overlying a top surface of said layer of porous material, each said band being bonded to said liquid-impervious layer.

18. A disposable absorbent product as defined in claim 17, wherein said bands are thermally bonded to said liquid-impervious layer.

19. A disposable absorbent product as defined in claim 1, wherein said secondary liquid containment structure includes projections extending laterally beyond respective side edges of said primary liquid-containment structure, said projections being foldable about edges of an undergarment to enhance a stability of said primary liquid-containment structure.

20. A disposable absorbent product as defined in claim 19, wherein said projections have zones covered with adhesive for releasably bonding said projections to a garment facing surface of the undergarment.

21. A disposable absorbent product as defined in claim 1, wherein said disposable absorbent product is selected from the group consisting of sanitary napkin, diaper, adult disposable brief and urinary pad.

22. A disposable absorbent product as defined in claim 19, wherein said disposable absorbent product is a sanitary napkin.

23. A disposable sanitary napkin, comprising:
a liquid-pervious cover layer for contacting a perineal region of the wearer:
an absorbent core underneath said liquid-pervious cover layer;
a liquid-impervious layer underneath said absorbent core, said liquid-impervious layer including longitudinally extending side edges;
the liquid-pervious cover layer and the liquid-impervious layer being joined to one another to completely enclose the absorbent core;
a secondary liquid containment structure including an elongate strip of absorbent material mounted underneath said liquid-impervious layer, said elongate strip of absorbent material being secured to said liquid-impervious layer adjacent to a center of said liquid-impervious layer, said strip of absorbent material being oriented generally transversally to a longitudinal axis of said liquid-impervious layer and projecting beyond respective side edges of said liquid-impervious layer to form liquid-acquisition zones capable of capturing body exudate leaking past either one of said side edges, a portion of said strip of absorbent material intermediate said liquid-acquisition zones constituting a reservoir area for collecting body exudate taken-up by said liquid-acquisition zones.

24. A disposable absorbent product, comprising:
a primary liquid-containment structure having longitudinally extending side edges and transversely extending end portions, said primary liquid-containment structure, including:
a) an absorbent core;
b) a liquid-impervious layer underneath said absorbent core;
a secondary liquid-containment structure secured underneath to said liquid-impervious layer at a location intermediate said transversely extending end portions, said secondary liquid-containment structure having a dimension measured along a longitudinal axis of said primary liquid-containment structure less than a longitudinal dimension of said primary liquid-containment structure, said secondary liquid-containment structure including:
a) a reservoir zone positioned underneath said liquid-impervious layer;
b) a pair of liquid-acquisition zones located in adjacency to respective longitudinally extending side edges of said primary liquid-containment structure, said liquid-acquisition zones being in liquid-communicative relationship with said reservoir zone, whereby said liquid-acquisition zones are capable of intercepting body exudate leaking past said side edges and then transfer the body exudate to said reservoir layer; and
c) longitudinal end portions of said secondary liquid-containment structure projecting beyond the longitudinal side edges of said primary liquid-containment structure, said longitudinal end portions being foldable about edges of an undergarment and providing means for enhancing a stability of said primary liquid-containment structure with relation to the undergarment; and
d) said liquid-acquisition zones being located on said longitudinal end portions.

25. A disposable absorbent product as defined in claim 24, comprising a capillary continuum between said liquid-acquisition zones and said reservoir zone, said capillary continuum allowing body exudate intercepted by said liquid-acquisition zones to migrate toward said reservoir zone.

26. A disposable absorbent product as defined in claim 25, wherein said secondary liquid-containment structure is bonded to said liquid-impervious layer at two sites in a spaced apart relationship.

27. A disposable absorbent product as defined in claim 26, wherein said capillary continuum passes between said sites.

28. A disposable absorbent product as defined in claim 24, comprising a layer of porous material underneath said liquid-impervious layer, a end portion of said layer of porous material constituting one of said liquid-acquisition zones, an area of said layer of porous material continuous with said end portion constituting said reservoir zone.

29. A disposable absorbent product as defined in claim 28, wherein said layer of porous material includes a localized area of reduced average pore size extending from one of said liquid-acquisition zones toward said reservoir zone, said localized area of reduced average pore size manifesting a high capillary attraction to induce liquid captured by said one liquid-acquisition zone to migrate toward said reservoir zone.

30. A disposable absorbent product as defined in claim 29, wherein said layer of porous material includes a densified region forming said localized area of reduced average pore size.

31. A disposable absorbent product as defined in claim 24, wherein said secondary liquid-containment structure includes a barrier layer underneath said reservoir zone.

32. A disposable absorbent product as defined in claim 24, wherein said longitudinal end portions have zones covered with adhesive for releasably bonding said longitudinal end portions to a garment facing surface of the undergarment.

* * * * *